(12) United States Patent
Janish et al.

(10) Patent No.: US 7,976,510 B2
(45) Date of Patent: Jul. 12, 2011

(54) SYRINGE WITH ADJUSTABLE TWO PIECE PLUNGER ROD

(75) Inventors: James Janish, Garfield, NJ (US); Mark Sebree, Mendham, NJ (US); Glenn D. Kopf, Fair Lawn, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 100 days.

(21) Appl. No.: 12/393,526

(22) Filed: Feb. 26, 2009

(65) Prior Publication Data

US 2009/0326479 A1 Dec. 31, 2009

Related U.S. Application Data

(60) Provisional application No. 61/032,182, filed on Feb. 28, 2008.

(51) Int. Cl.
A61M 5/315 (2006.01)

(52) U.S. Cl. ......................................................... 604/218

(58) Field of Classification Search .......... 604/218–231, 604/181, 187, 192–198, 110
See application file for complete search history.

(56) References Cited

U.S. PATENT DOCUMENTS

| | | | |
|---|---|---|---|
| 2,129,675 A * | 9/1938 | Cole | 604/211 |
| 2,283,915 A * | 5/1942 | Cole | 604/211 |
| 2,658,511 A * | 11/1953 | Furnell | 604/218 |
| 3,232,117 A * | 2/1966 | Gilmont | 73/864.13 |
| 3,506,008 A | 4/1970 | Huck | |
| 3,840,007 A | 10/1974 | Fish | |
| 4,390,016 A | 6/1983 | Riess | |
| 4,444,335 A * | 4/1984 | Wood et al. | 222/43 |
| 4,498,904 A * | 2/1985 | Turner et al. | 604/211 |
| 4,636,202 A | 1/1987 | Lowin et al. | |
| 4,650,468 A * | 3/1987 | Jennings, Jr. | 604/110 |
| 4,654,035 A * | 3/1987 | Ando | 604/210 |
| 4,790,822 A | 12/1988 | Haining | |
| 4,950,251 A | 8/1990 | Haining | |
| 5,135,495 A | 8/1992 | Arcusin | |
| 5,152,750 A | 10/1992 | Haining | |
| 5,222,942 A | 6/1993 | Bader | |

(Continued)

FOREIGN PATENT DOCUMENTS

DE 102005019428 10/2006

(Continued)

OTHER PUBLICATIONS

International Search Report dated May 6, 2009 (PCT/US2009/035442).

(Continued)

*Primary Examiner* — Kevin C Sirmons
*Assistant Examiner* — Michael J Anderson
(74) *Attorney, Agent, or Firm* — The Webb Law Firm; James J. Murtha

(57) ABSTRACT

Medical devices comprising a syringe barrel and a two-piece plunger rod are provided. According to one or more embodiments, the two-piece plunger rod includes a distal portion and proximal portion slidably mounted to the distal portion. The distal and proximal portions include a tab and plurality of grooves which engage to adjust the overall length of the plunger rod to a plurality of locked lengths. The locked lengths of the plunger rod permit varying amount of fluid to be expelled from the barrel.

18 Claims, 17 Drawing Sheets

U.S. PATENT DOCUMENTS

| | | | |
|---|---|---|---|
| 5,226,896 A | 7/1993 | Harris | |
| 5,253,785 A | 10/1993 | Haber et al. | |
| 5,318,544 A | 6/1994 | Drypen et al. | |
| 5,344,403 A | 9/1994 | Lee | |
| 5,385,558 A * | 1/1995 | Cottone et al. | 604/208 |
| 5,411,489 A | 5/1995 | Pagay et al. | |
| 5,531,708 A | 7/1996 | Woodruff | |
| 6,086,567 A | 7/2000 | Kirchhofer et al. | |
| 6,494,863 B1 | 12/2002 | Shaw et al. | |
| 6,583,930 B1 | 6/2003 | Schrenk et al. | |
| 2005/0215957 A1 | 9/2005 | Hynes | |
| 2006/0229570 A1 | 10/2006 | Lovell et al. | |
| 2007/0017532 A1 | 1/2007 | Wyrick | |
| 2007/0017533 A1 | 1/2007 | Wyrick | |
| 2007/0244444 A1 | 10/2007 | Guelker et al. | |
| 2008/0015514 A1 | 1/2008 | Burren et al. | |
| 2008/0177236 A1 | 7/2008 | Burren et al. | |
| 2009/0177156 A1 * | 7/2009 | MacLean | 604/135 |

FOREIGN PATENT DOCUMENTS

| | | |
|---|---|---|
| DE | 102005019428 A1 | 10/2006 |
| EP | 1323450 A1 | 12/2001 |
| EP | 1323450 A1 | 7/2003 |
| EP | 1518574 A2 | 3/2005 |
| WO | 2003020347 A2 | 3/2003 |
| WO | WO-03/020347 A2 | 3/2003 |
| WO | 2005011782 A1 | 2/2005 |
| WO | WO-2005/011782 A1 | 2/2005 |
| WO | 2006136769 A1 | 12/2006 |
| WO | WO-2006/136769 A1 | 12/2006 |
| WO | 2007109450 A2 | 9/2007 |
| WO | WO-2007/109450 A2 | 9/2007 |
| WO | WO-2008/068502 A1 | 6/2008 |
| WO | 2008068502 A1 | 3/2010 |

OTHER PUBLICATIONS

International Search Report dated Jun. 18, 2009 (PCT/US2009/035493).

PCT ISR and Written Opinion for PCT/US2009/035442, (Jun. 5, 2009), 15 pgs.

PCT ISR & Written Opinion for PCT/US2009/035493, (Jun. 18, 2009), 15 pgs.

U.S. Appl. No. 12/393,800, filed Feb. 26, 2009.

* cited by examiner

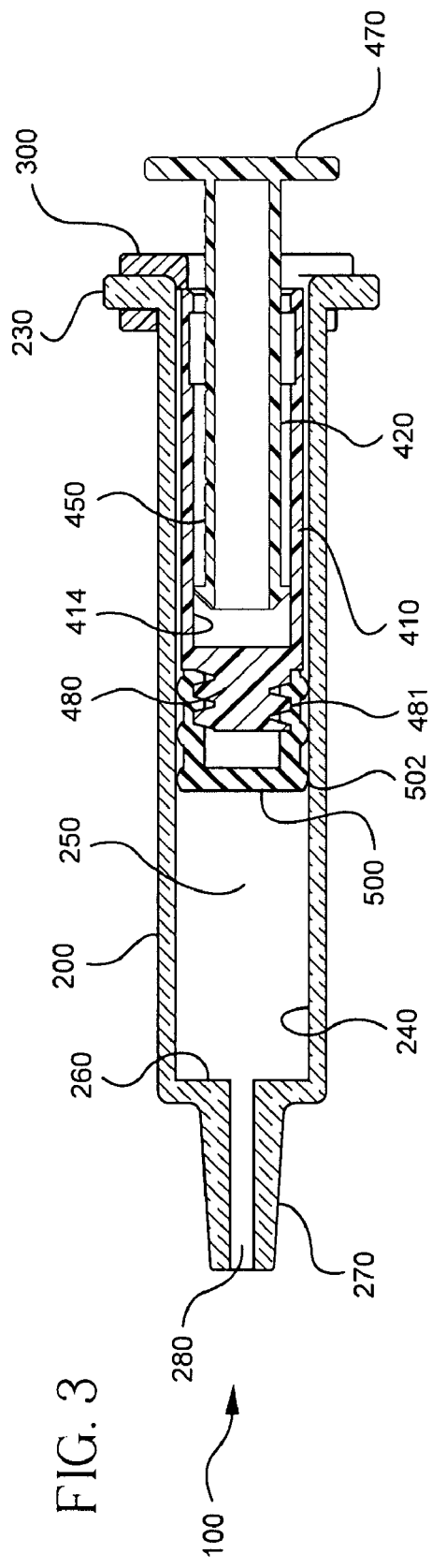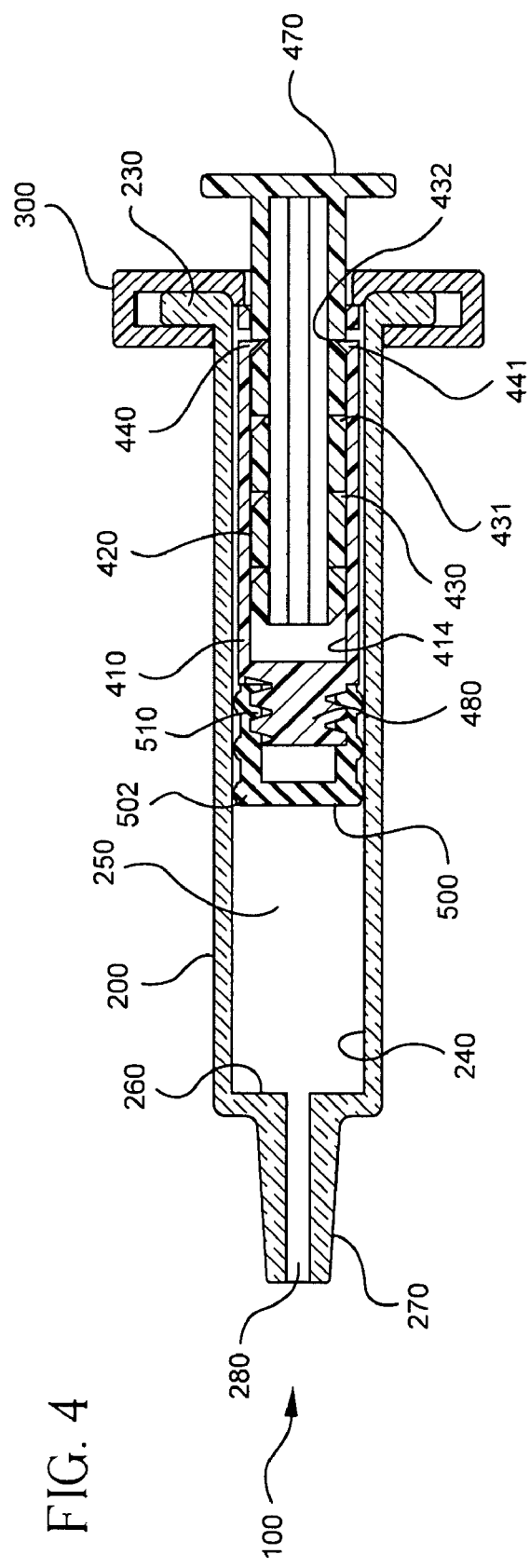

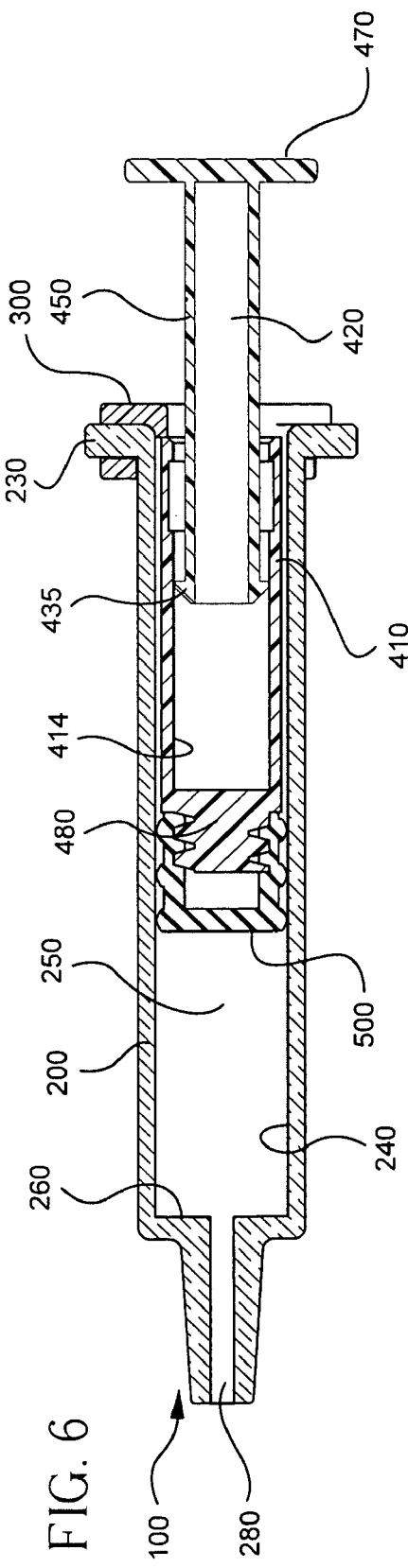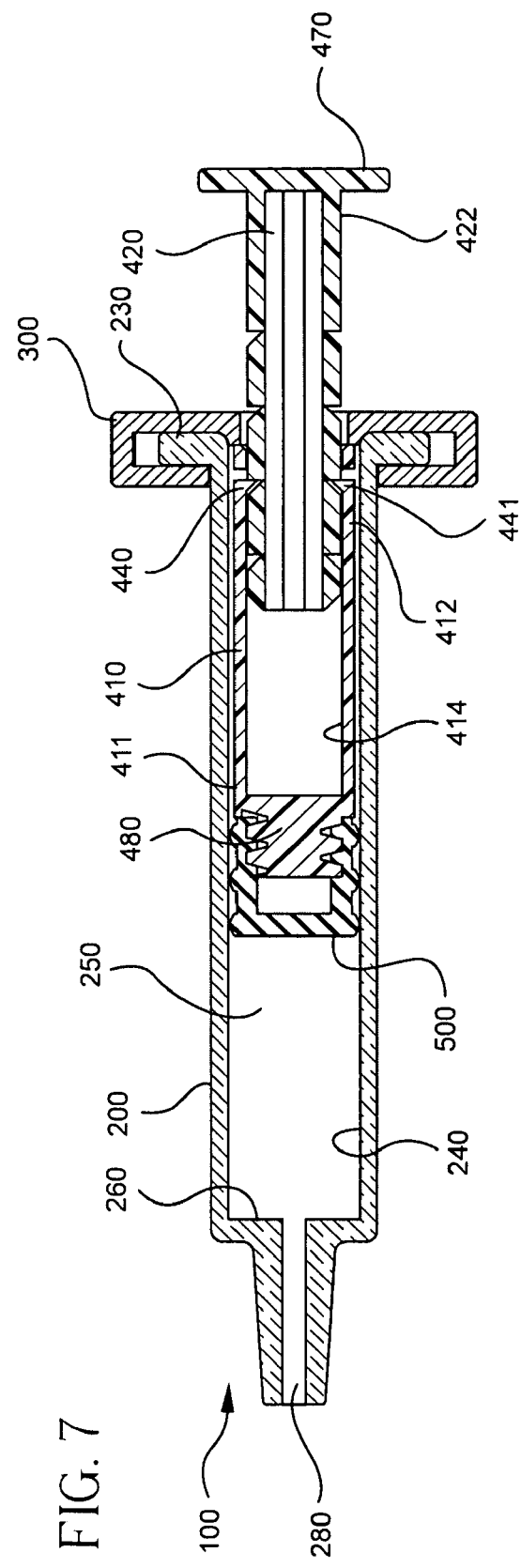

SYRINGE WITH ADJUSTABLE TWO PIECE PLUNGER ROD

CROSS REFERENCE OF RELATED APPLICATION

This application claims the benefit of priority under 35 U.S.C. §119(e) to U.S. Patent Application No. 61/032,182, filed Feb. 28, 2008, which is hereby incorporated by reference in its entirety.

TECHNICAL FIELD

The present invention relates to medical devices having a syringe barrel and a two-piece plunger rod which allows its length to be adjusted.

BACKGROUND

Syringes generally comprise an elongate single piece plunger rod disposed in a barrel. Generally, the plunger rod is of one piece construction. Syringes that have breakable plunger rods, which break upon application of force into two or more piece, have been used to prevent reuse of syringes. However, such syringes in which the plunger rod breaks into pieces render the syringe assembly inoperable because the plunger rod can no longer be advanced within the barrel of the syringe.

In applications where the syringe is prefilled with fluid and then packaged for delivery to the user, the length of the single piece plunger rod must at least long enough to accommodate the full length of the barrel. Such prefilled syringes act as the storage container for the fluid and must be packaged in such a way to accommodate the prefilled syringe barrel and its full length single piece plunger rod.

While there are a variety of syringe designs available, alternative and improved syringe and plunger rod designs are always desired for various applications and to reduce costs associated with manufacturing and packaging of medical devices.

SUMMARY

In this disclosure, a convention is followed wherein the distal end of the device is the end closest to a patient and the proximal end of the device is the end away from the patient and closest to a practitioner.

One aspect of the present invention pertains to a medical device including an elongate two-piece plunger rod for use within the syringe barrel. According to one or more embodiments, the syringe barrel has a side wall with an inside surface defining chamber for retaining fluid. The syringe barrel has an open proximal end which includes a peripheral flange and distal end which includes a distal wall. The distal wall has a passageway or opening therethrough in fluid communication with the chamber. In at least one embodiment, the chamber is pre-filled with a fluid. In one embodiment, the fluid is a flush solution. In another embodiment, the fluid includes medication.

In one or more embodiments, an elongate plunger rod has an overall length that can be adjusted and is extendible to a plurality of locked lengths. In accordance with one or more embodiments, the plunger rod has a distal end and a proximal end, wherein a stopper having a distal face is attached to the distal end and a thumbpress is attached to the proximal end. According to one embodiment, a thumbpress cap is provided which covers the thumbpress of the plunger rod. The thumbpress cap of one or more embodiments is adapted to lock with the peripheral flange or otherwise form a seal with the peripheral flange.

The plunger rod according to one embodiment is made up of a distal portion and a proximal portion, where the proximal portion is slidably mounted to the distal portion and allows the overall length plunger rod to be adjusted and are disposed in a slidably moveable relationship so the plunger rod has an adjustable length which is extendible to a plurality of locked lengths. As used herein, the distal portion and the proximal portion of the plunger rod may also be referred to herein as the first distal portion and the second proximal portion, respectively. A thumb press may be associated with the proximal portion and a stopper may be associated with the distal portion. The proximal portion slidably receives the distal portion in one embodiment. In another embodiment, the distal portion slidably receives the proximal portion. In some embodiments, the proximal portion is hollow and the distal portion has a size and shape which allows it to be inserted into the hollow proximal portion. In other embodiments, the distal portion is hollow and the proximal portion is sized to be inserted into the hollow distal portion. Embodiments having a hollow distal portion also include a tab disposed thereon and a plurality of depressions disposed axially along the length of the proximal portion which cooperate with the tab to form a plurality of locked positions. In another embodiment, the depressions disposed on the proximal portion are notches with a ramped surface and a stop face, which engages the tab when the plunger rod is in a locked position.

The plurality of locked positions permits varying amounts of fluid to be expelled from the barrel in accordance with one embodiment. The medical device of a further embodiment includes indicia of the amount of fluid to be dispensed from the syringe when the plunger rod is advanced distally and prevented from further distal movement. In another embodiment, the indicia provide the amount of fluid dispensed when the plunger is advanced from a selected locked length.

In one embodiment, the plunger rod is sized to have a length that allows the distal face of the stopper to contact the distal wall of the syringe barrel when the plunger rod is advanced distally in a fully extended locked length. In one embodiment, the distal face of the stopper does not contact the distal wall of the syringe barrel when the plunger rod is advanced distally in a locked length that is less than the fully extended locked length. In this configuration, when the thumbpress is advanced distally, the thumb press or a distal portion of the plunger rod encounters resistance against the proximal portion of the barrel that prevents further distal movement of the plunger rod in the barrel. In another embodiment, the device includes one or more intermediate locked lengths, which allow varying amounts of fluid to be expelled from the syringe.

In accordance with one or more embodiments, the distal portion and proximal portion can be rotated with respect to each other in rotational positions. The distal portion and proximal portion can be rotated to a first rotation position which allows axial movement of the distal and proximal portions of the plunger rod. In another embodiment, the distal and proximal portions can be rotated to a second rotation position, which allows the distal and proximal portions of the plunger rod to lock and restricts relative axial movement thereof. The first rotation and second rotation positions differ by about 90 degrees in one embodiment.

Another aspect of the invention pertains to a medical device with a syringe barrel having an elongate plunger rod disposed therein, the plunger rod including a distal portion and a proximal portion arranged in a slidable, nested arrangement. The syringe barrel has a side wall with an inside surface defining chamber for retaining fluid and an open proximal end and distal end which includes a distal wall with a passageway or opening therethrough in fluid communication with the chamber. The chamber of at least one embodiment is pre-filled with a fluid such as a flush solution or a medication. One embodiment provides for a medical device enclosed in a package.

Another aspect of the invention is that the distal and proximal portions of the plunger rod include a plurality of grooves and a projecting tab which cooperates with the grooves to provide the plunger rod with an adjustable overall length which is extendible to a plurality of different locked lengths. The grooves may be spaced axially along the proximal portion of the plunger rod and the tab may be disposed on the distal portion. Further embodiments include indicia associated with each groove to indicate the amount of fluid that will be expelled from the syringe when the plunger rod is fully advanced distally until it is stopped from further distal movement. As will be understood further below, in one embodiment, when the plunger rod is in the extended or fully extended position, the plunger rod is prevented from further distal movement when the distal face of the stopper bottoms out and contacts the distal wall of the syringe barrel. In the compressed position and in one or more intermediate positions, the stopper on the distal end of the plunger rod does not bottom out, and further distal movement of the plunger rod in the barrel is prevented when the plunger rod is stopped against the barrel, typically when the thumb press encounters the proximal end of the barrel or when some other stop prevent further distal movement of the plunger rod. In another embodiment, the indicia provide the amount of fluid that will be expelled from the syringe when the plunger rod having one or more adjusted locked lengths is fully advanced distally.

Another aspect of the invention is a tab that comprises radially inward projections which fit into the grooves to prevent relative axial movement of the distal and proximal portions of the plunger rod. According to another embodiment, the proximal portion includes an axially extending narrowed portion, which permits the tab to slide along the proximal portion and allows the distal and proximal portion to be fully extended and compressed with respect to each other. In at last one embodiment, the axially extending narrowed portion allows the tab to engage at least one of the grooves upon rotation of the proximal portion with respect to the distal portion.

Another aspect of the invention pertains to a medical device including an elongate plunger rod disposed in a syringe barrel, the plunger rod including a distal portion and a proximal portion being slidable with respect to each other. In one embodiment, the syringe barrel has a side wall with an inside surface defining chamber for retaining fluid. In one embodiment, the syringe barrel has an open proximal end and distal end which includes a distal wall. The distal wall has a passageway or opening therethrough in fluid communication with the chamber. The chamber of at least one embodiment is pre-filled with a fluid. In one embodiment, the fluid is a flush solution. In another embodiment, the fluid includes medication. One or more embodiments of the present invention include a means for regulating the length of the plunger rod to permit variable amounts of fluid to be expelled from the syringe.

One of the advantages of the present invention is that it allows the syringe barrel to be prefilled with medication and packaged with the plunger rod, in its compressed stated thereby utilizing less packaging material. This results in a lower cost device which requires less space for storage.

Another aspect of the invention is that the adjustable plunger rod allows a user to adjust the amount of medication to dispense based on the patient's requirement.

BRIEF DESCRIPTION OF THE DRAWINGS

FIG. 3 shows a cross-sectional view taken along line 3-3 of FIG. 1;

FIG. 4 shows a cross-sectional view taken along line 4-4 of FIG. 1;

FIG. 6 shows a cross-sectional view taken along line 6-6 of FIG. 5;

FIG. 7 shows a cross-sectional perspective view taken along line 7-7 of FIG. 6;

DETAILED DESCRIPTION

Figure 1:
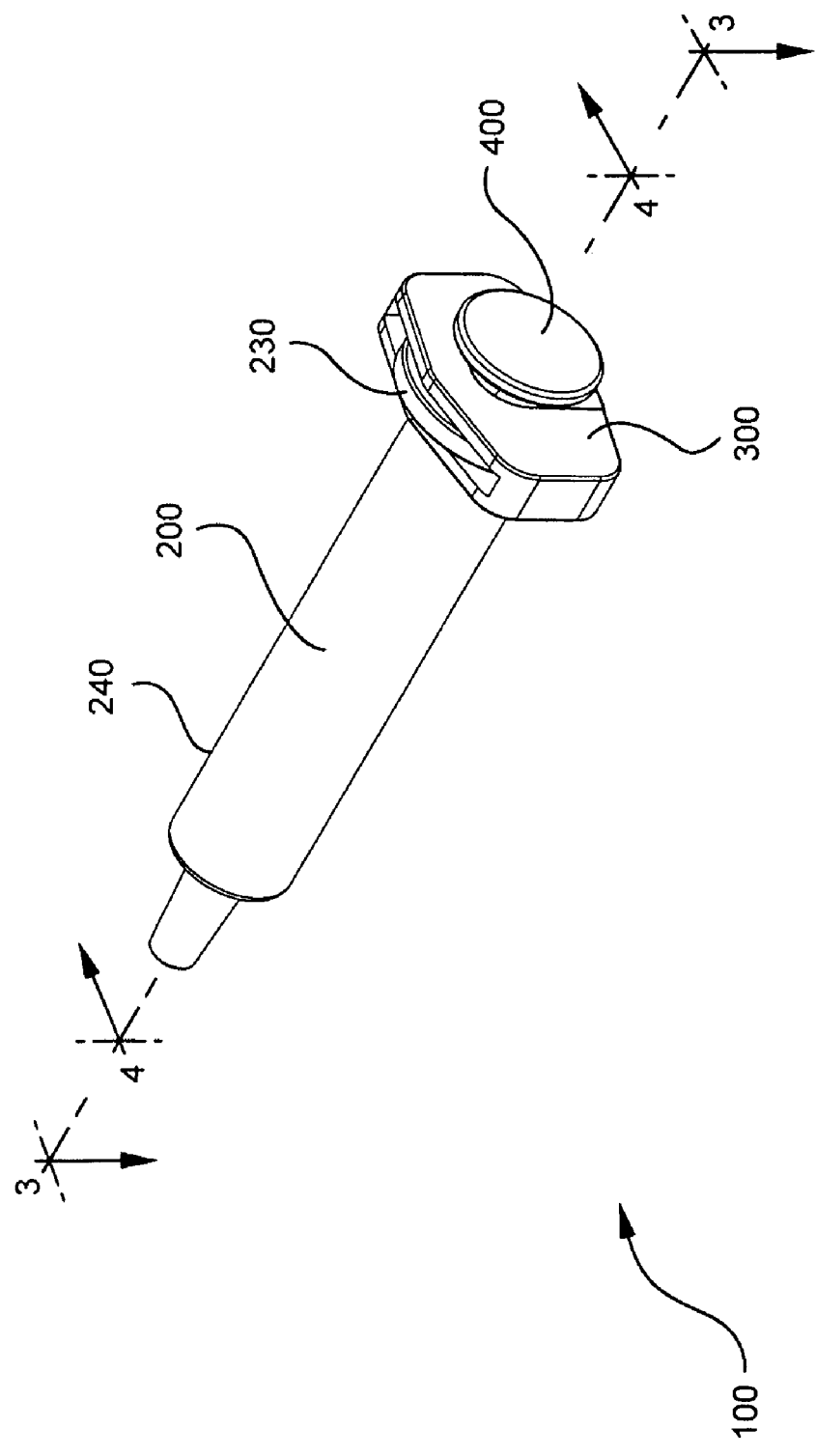
FIG. 1 illustrates a perspective view of a medical device in a compressed position according to an embodiment of the invention.

Before describing several exemplary embodiments of the invention, it is to be understood that the invention is not limited to the details of construction or process steps set forth in the following description. The invention is capable of other embodiments and of being practiced or being carried out in various ways.

One aspect of the present invention provides for an article or medical device including a syringe barrel and a plunger rod comprising two pieces. The plunger rod of one or more embodiments has a proximal end and a distal end which includes a stopper on the distal end and thumb press on the proximal end. The plunger rod further includes a distal portion and a proximal portion disposed in a slidable arrangement to permit adjustment of the plunger rod length to a plurality of different locked lengths, which, in turn allows different amount of fluid to be expelled from the syringe.

FIGS. 1-8 show a medical device 100 in the form of a syringe assembly comprising a syringe barrel 200 and a plunger rod 400. The syringe barrel 200 includes a peripheral flange 230 at the proximal end 220 of the syringe barrel 200, which provides the practitioner a gripping surface for the barrel 200 when fluid is being expelled from the syringe. The device also includes a flange sleeve 300 in the embodiment shown. The flange sleeve 300 attaches to the barrel 200 to provide protection of the peripheral flange 230 and enhance the gripping surface of the barrel 200 when the fluid is being expelled from the syringe. The syringe barrel 200 has a distal end 210 and a proximal end 220, and a cylindrical inside surface 240, which defines a chamber 250 in which fluid may be held. The syringe barrel further includes a distal wall 260 having a passageway or opening 280 in fluid communication with the chamber. The passageway of opening 280 can also include a tip 270 or reduced diameter portion. Further embodiments of the invention include a protective cap (not shown) to cover the tip 270. One embodiment can include a collar (not shown) which can provide a means for attaching a cap or a needle to the syringe barrel. Such an attachment means may be, for example, a luer-lock collar. As the skilled artisan will understand, the syringe barrel according to certain embodiments may further include a needle hub and needle cannula (not shown) having a lumen attached to a collar (not shown) or tip 270. Such a device including a needle hub and cannula would also include a protective cap (not shown) over the needle cannula. Further examples can include a seal or other means for detecting tampering on the collar, cap and/or syringe barrel.

Plunger rod 400 includes a distal portion 410 and a proximal portion 420 which are assembled together, as will be described in more detail below. The plunger rod may be disposed within the chamber 250 for sliding sealed engagement with the inside surface 240 of the syringe barrel 200. The plunger rod 400 includes a distal end 403 and a proximal end 405. A stopper 500 may connected to the distal end 403 of the plunger rod. It will be understood that the stopper 500 may be integral with the plunger rod, or it may be provided as a separate component that is releasably mounted to the plunger rod 400, as shown in the Figures.

The distal end 403 of the plunger rod 400 includes stopper attachment member 480 for releasably attaching a stopper 500 to the plunger rod 400. The stopper attachment member 480 shown in the Figure may be, for example, stopper attachment threads 481. The stopper 500 may also include corresponding stopper threads 510, permitting the stopper 500 to be assembled to the plunger rod 400 using a twisting motion. It will be understood that any other suitable releasable attachment mechanism could be used to attach the stopper to the plunger rod. In one embodiment, the stopper attachment member 480 of the plunger rod 400 comprises a male joint while the stopper 500 comprises a female joint. In another embodiment, the stopper 500 is a male joint while the stopper attachment means 480 is a female joint. The stopper 500 can also include a sealing element, such as ribs, 502 forming a seal with the inside surface of the syringe barrel 200.

The proximal portion 420 of the plunger rod 400 includes a distal end 421, a proximal end 422, and thumb press 470 attached at its proximal end 422. One or more embodiments of the present invention provide for a thumb press having a textured surface, which may provide an enhanced surface for a user of the syringe to exert distally directed force on the plunger rod to advance the plunger rod into the barrel and expel fluid from the syringe.

The distal portion 410 of the plunger rod 400 comprises a distal end 411 and a proximal end 412. The distal portion 410 comprises a frame 413 defining a hollow receptacle 414. The proximal portion 420 also has a complementary frame 423 shaped identically in cross section to the distal portion 410 and is sized and shaped to allow the distal portion 410 to operate as the female joint and the proximal portion 420 to operate as the male joint that fits in the hollow receptacle 414 of the distal portion 410. This allows the proximal portion 420 to slide proximally and distally when disposed within the hollow receptacle 414 of the distal portion 410. It will be understood that the complimentary frame 423 does not have to be shaped identically in cross section to the frame 413 of the distal portion. For example, while the distal portion frame 413 is "T" or shaped in the form of a cross, the proximal portion frame 423 may be any suitable shape that allows it to slidably received within the frame 413, for example, an "L" shape, or "V" shape or a single blade that fits within one of the channel of the distal portion hollow frame 413.

In one or more embodiments, the frame 413 is shaped to prevent rotational movement of the distal and proximal portions 410, 420. In one embodiment, the frame 413 is shaped to prevent such rotational movement beyond a predetermined position. In alternative embodiments, the frame 413 may be shaped in the form of a square, rectangle, triangle of any other shape suitable for a plunger rod. Further embodiments provide for a frame 413 that includes a mechanism or means for preventing rotational movement of the distal portion 410 or the proximal portion 420 of the plunger rod 400 beyond a predetermined position. In one embodiment, the predetermined position within which the distal and proximal portions 410, 420 are permitted rotational movement includes the first rotation position and the second rotation position, as will be defined herein.

As specifically shown in FIGS. 3 and 4, the proximal portion 420 fits inside the hollow receptacle 414 of the distal portion 410. It will be understood, of course, that the invention is not limited to the configuration shown. For example, the configuration could be reversed, and proximal portion 420 can comprise a frame defining hollow receptacle and operate as the female joint, while a distal portion comprises a complementary frame and operates as the male joint that fits into the hollow receptacle.

Figure 2:
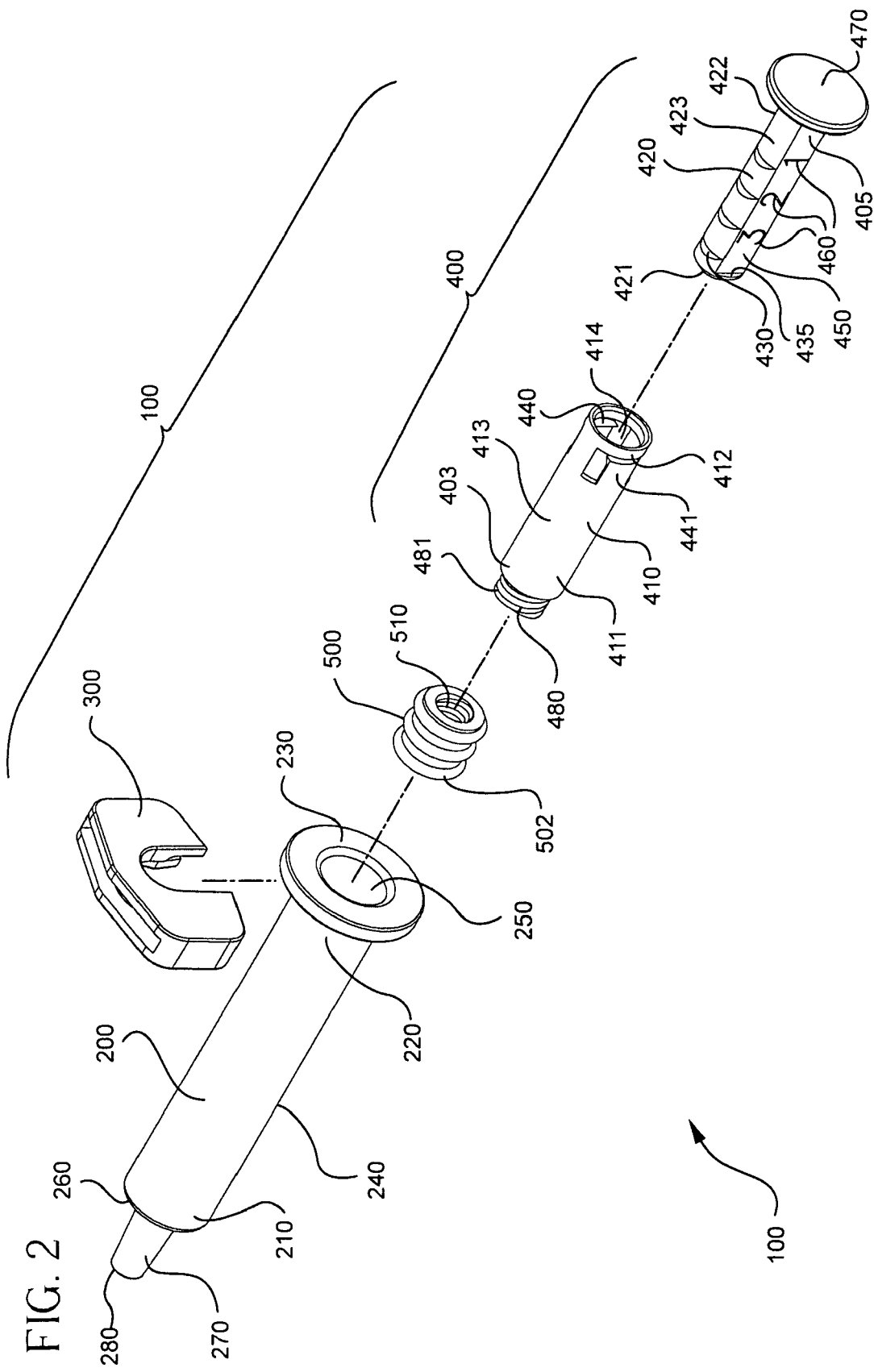
FIG. 2 illustrates a disassembled perspective view of a medical device according to an embodiment of the invention.
Figure 5:
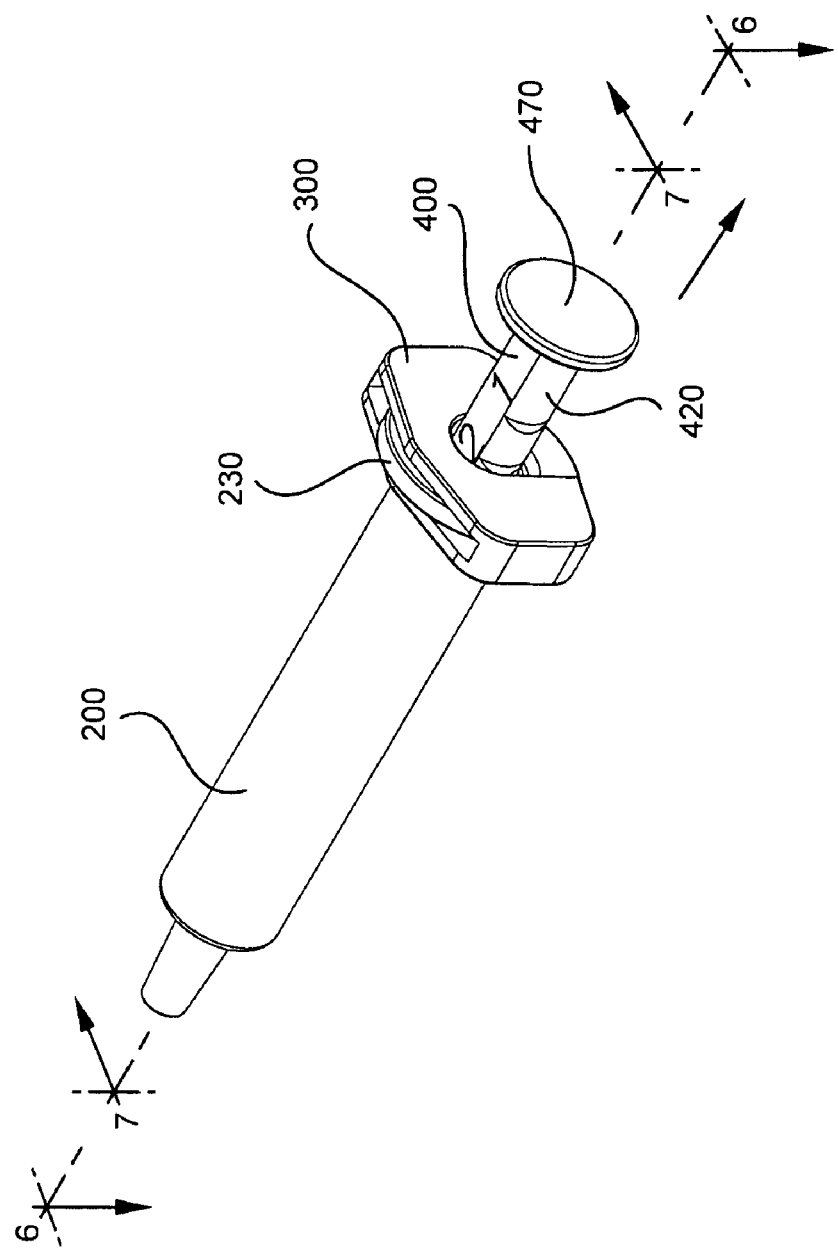
FIG. 5 illustrates a perspective view of an embodiment of the medical device wherein the plunger rod is positioned to an extended length.
Figure 8:
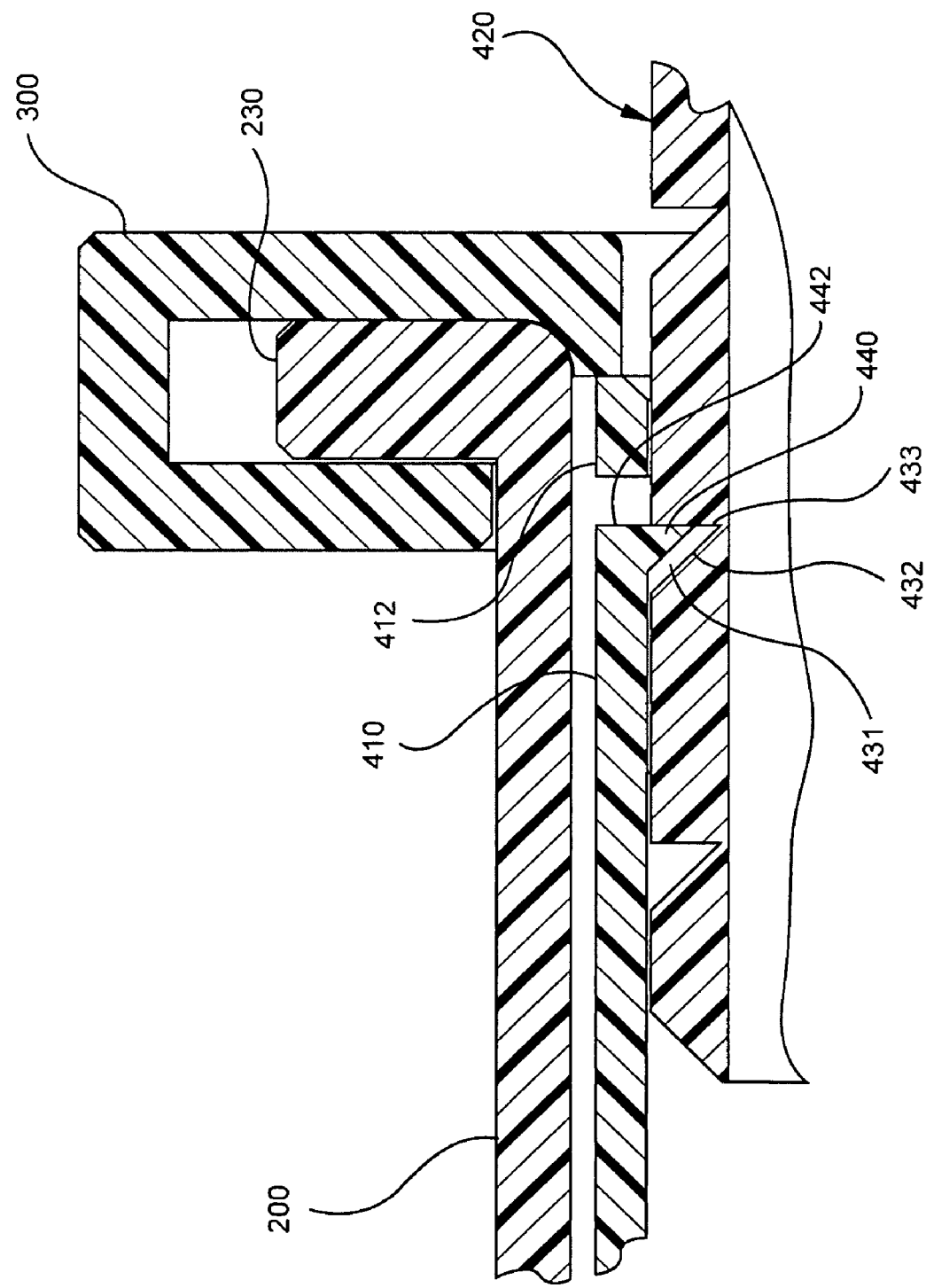
FIG. 8 is an enlarged view of a portion of FIG. 7.

In the embodiment shown in FIG. 2, the distal portion 410 of the plunger rod 400 has a tab in the form of two radially inward projections 440, 441 disposed near its proximal end 412. In accordance with alternative embodiments, the tab can also be disposed near the distal end 411 of the distal portion 410. In further embodiments, the tab can extend radially and outwardly from the frame 413 of the distal portion 410. In one or more embodiment, the tab is flexible and biased radially inwardly against a surface of the proximal portion 420 to limit relative axial movement of the distal portion 410 and proximal portion 420.

In the embodiment shown in FIGS. 1-4, the proximal portion 420 has a plurality of grooves 430 disposed on an axial portion of its complementary frame 423. In the embodiment shown, the grooves 430 are disposed at regular intervals from the distal end 421 to the proximal end 422 of the proximal portion 420. In one embodiment, each groove disposed on the proximal portion represents a different length or intermediate locked lengths to which the plunger rod can be adjusted. As will be discussed in further detail, the radially inward projections 440, 441 of the distal portion 410 cooperate with the grooves 430 of the proximal portion 420 to permit adjustment of the plunger rod length. A skilled artisan will recognize that structures other than the radially inward projections 440, 441 and plurality of axially spaced cooperating grooves 430 disposed could perform this function. An alternative embodiment is shown in FIGS. 9-12 and discussed further below. As more clearly shown in FIG. 8, the grooves 430 include a notch 431 having a ramped surface 432 positioned at an angle from the complementary frame 423 of the proximal portion 420. The notch further includes a stop face 433 positioned perpendicularly to the complementary frame 423 of the proximal portion 420. The projections 440, 441 include a perpendicular face 442. To engage with one of the grooves 430, the projections 440, 441 enter the notch 431, whereby the perpendicular face 442 can contact the stop face 433. Upon application of a distally directed force, the perpendicular face 442 and the stop face 433 meet and prevent relative movement between the distal portion 410 and the proximal portion 420 and allows the length of the plunger rod to remain fixed as will be more fully discussed.

The complementary frame 423 of the proximal portion 420 also includes an axially extending narrowed portion 450, which also includes indicia 460 disposed thereon. The indicia 460 in the embodiment shown correspond to the grooves 430 disposed on the complementary frame 423 of the proximal portion 420. In another embodiment, the indicia 460 may also be disposed on the axial portion of the complementary frame which includes the plurality of grooves 430. In the embodiment shown, the proximal portion 420 can include a distal lip 435 at its distal end 421, which prevents the distal portion 410 and proximal portion 420 from being separated from each other.

In one embodiment, the grooves 430 are axially disposed on one-half of the surface of the complementary frame while the other one-half of the surface of the complementary frame comprises the axially extending narrowed portion. An alternative embodiment provides for alternating the axially extending narrowed portions of the complementary frame with the portions comprising grooves. In such embodiments, the tab or projections of the distal portion 410 would be positioned to permit engagement with the grooves.

In use, with reference with FIGS. 3-9, the projections 440, 441 engage at least one of the grooves 430 disposed on the proximal portion 420. For example, FIGS. 3 and 4 show the projections 440, 441 engaged with one of the grooves 430 disposed near the proximal end 422 of the proximal portion 420. FIGS. 6 and 7 also show such engagement wherein the projections 440, 441 is engaged with one or more of the grooves 430 disposed near the distal end 421 of the proximal portion 420. The cooperation of the projections 440, 441 and the grooves 430 operate to prevent the distal and the proximal portions 410, 420 from unintentionally sliding with respect to each other.

To assemble the plunger rod to the shortest length or a compressed state or to assemble the medical device for packaging, as shown in FIG. 3, the proximal portion 420 is fully inserted into the hollow receptacle 414 of the distal portion 410 by aligning the projections 440, 441 so it rests on the axially extending narrowed portion 450 of the proximal portion 420. This positioning allows the projections 440, 441 of the distal portion 410 to advance in the proximal direction without engaging with one or more of the grooves 430 of the proximal portion 420. Once the proximal portion 420 is fully inserted inside the hollow receptacle 414 of the distal portion 410, the proximal portion 420 can be rotated to so that one or more of grooves 430 disposed near the proximal end 422 of the proximal portion 420 engage with projections 440, 441. In one or more embodiments, the proximal portion 420 includes one or more locking grooves (not shown) disposed near its proximal end 422 which engage the projections 440, 441 of the distal portion 410 to releasably lock the plunger rod 400 in a compressed state.

For use with the syringe assembly, a stopper 500 is attached to the distal end of the distal portion 410 of the plunger rod 400. The plunger rod-stopper assembly is then inserted within the chamber 250 of the syringe barrel 200 at its proximal end 220.

To deploy the plunger rod into a fully extended or intermediate position or to adjust the length of the plunger rod, as shown in FIGS. 5-9, the practitioner or user applies a force in the proximal direction to the proximal portion 420 of the plunger rod 400. The projections 440, 441 of the proximal portion 420 move past the grooves 430 until the proximal portion 420 is extended out of the distal portion 410 to a desired position, or the plunger rod 400 is extended to a desired length. The grooves 430 and projections 440, 441 are adapted to allow proximal movement of the proximal portion 420 relative to the distal portion, as more fully described with reference to FIG. 8.

The length of the plunger rod in any embodiment described herein can be adjusted without rotational movements. The plunger rod and its components described herein are flexible enough to withstand adjustment of the length of the plunger rod without the use of rotational movements. In one or more embodiments, rotational movements are used solely during assembly of the medical devices described herein.

As otherwise stated, the grooves 430 represent the different locked lengths to which the plunger rod can be adjusted. The locked lengths represent the amount of fluid in the syringe barrel that can be expelled. In one embodiment, engaging the projections 440, 441 with one or more selected grooves 430 effectively measures and sets the amount of fluid to be expelled.

Figure 9:
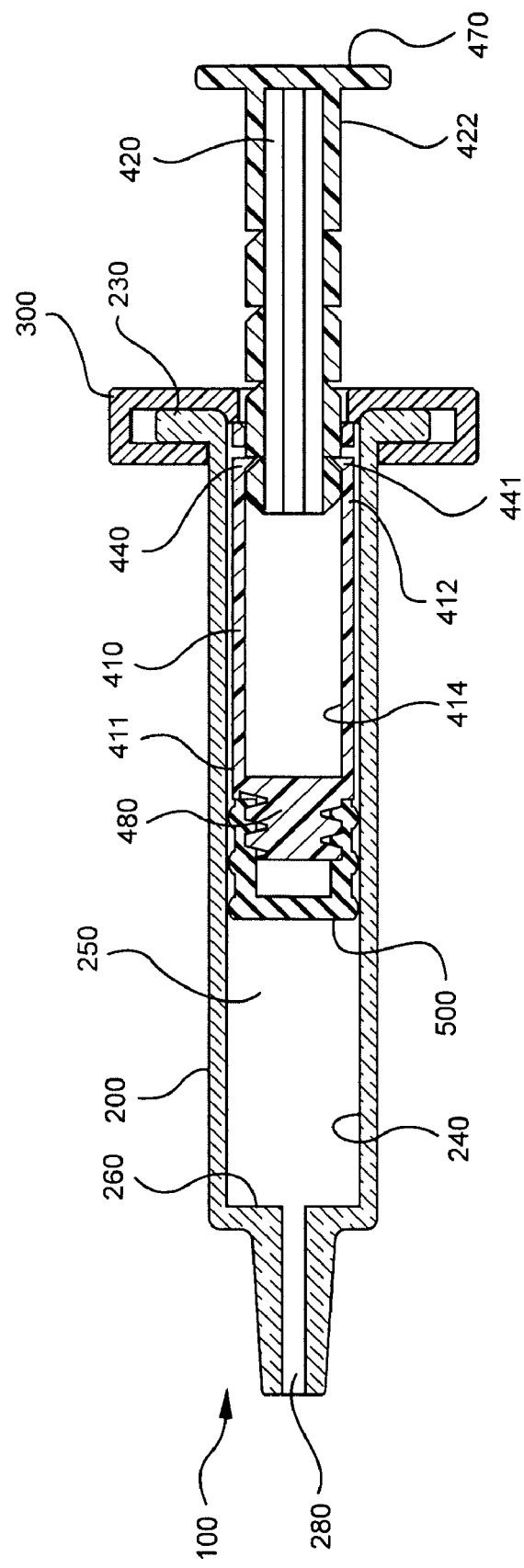
FIG. 9 shows the embodiment of FIG. 7 in a fully extended length.

In the fully compressed state or at intermediate lengths, as shown in FIGS. 3 and 4, the peripheral flange 230 of the barrel 200 prevents movement of the plunger rod 400 in the distal direction by blocking the thumbpress 470 when a distally directed force is applied to the plunger rod. In the fully extended state, as shown in FIG. 9, an application of a distally directed force on the plunger rod 400 allows movement in the distal direction until the stopper 500 contacts the distal wall 260 of the barrel 200.

As shown in the Figures, the distal portion of the distal portion 410 and the proximal portion 420 overlap when the plunger rod is adjusted to an extended or intermediate locked length or position. The overlap provides stability to the two-piece plunger rod when the plunger rod is being advanced distally into the barrel of the syringe. The syringe shown in FIGS. 6 and 7 is now ready for use by applying a distally directed force to the thumb press to move the plunger rod 400 through the barrel 200 of the syringe to expel fluid from the syringe.

An alternative embodiment is shown in FIGS. 10-13. The alternative embodiment which shows substitute structures disposed on distal and proximal portions 610, 620, which engage to adjust the length of the plunger rod 600. A plurality of depressions or stops 630 are spaced axially along the proximal portion. The proximal portion 620 according to the embodiment shown includes a continuous axial indentation 635 disposed along the length of the second plunger rod 620 and a thumbpress 670 at the proximal end of the proximal portion 620. In one embodiment, the proximal portion 620 has more than one continuous axial indentation or track 635 disposed thereon. In the embodiment shown, the indentation or track 635 bisects the depressions or stops 630. The proximal portion 420 further includes an narrowed portion 650, which also includes indicia or markers 660 disposed thereon for indicating the amount of fluid expelled from the syringe when operated from a particular stop 630. The markers 660 in the embodiment shown correspond to the depressions or stops 630 disposed on the axial portion of the proximal portion 620. The second proximal position further includes a locking depression 631 near its proximal end 621.

The distal portion 610 of the alternate embodiment shown in FIGS. 10-13 includes complementary protrusions 640, 641 at its distal end 612, which cooperate with a rib 680 on the proximal portion 620 to prevent accidental separation of the plunger rod portions 610, 620. The distal portion also includes radially inward detents 643, 644. In one embodiment, the indentation or track 635 guides alignment of the detents 643, 644 for assembly of the device. In another embodiment, detents 643, 644 fit within the indentation or track 635 and guide the distal and proximal portions 610, 620 when adjusting the length of the plunger rod 400.

Figure 10:
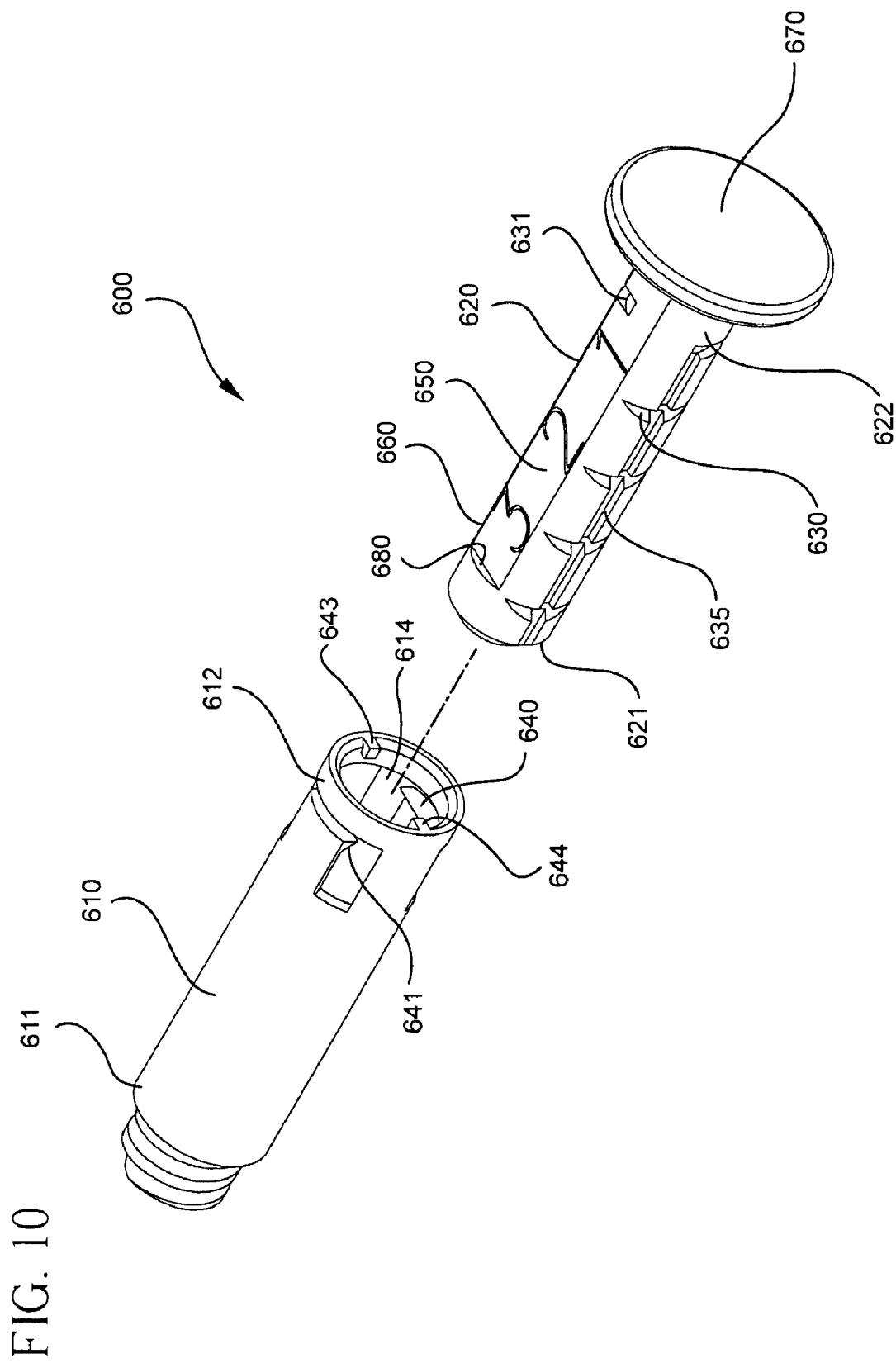
FIG. 10 illustrates a disassembled perspective view of a medical device according to a second embodiment of the invention.
Figure 11:
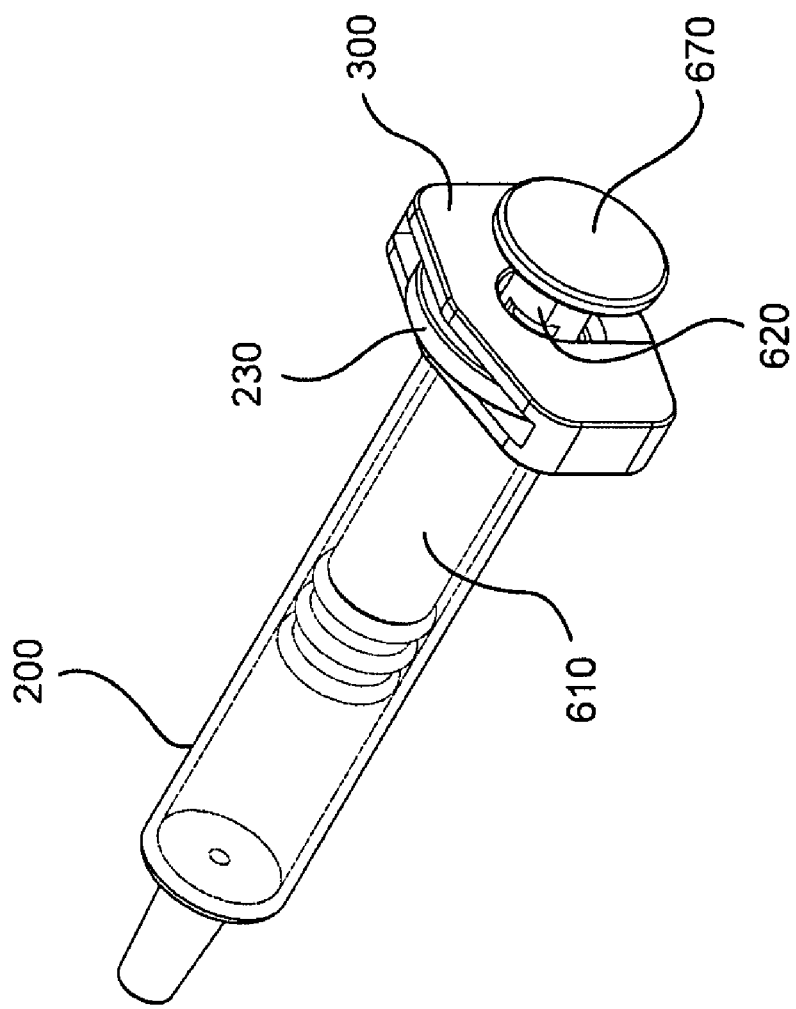
FIG. 11 illustrates a perspective view of a second embodiment of the medical device wherein the plunger rod is positioned to compressed length.
Figure 12:
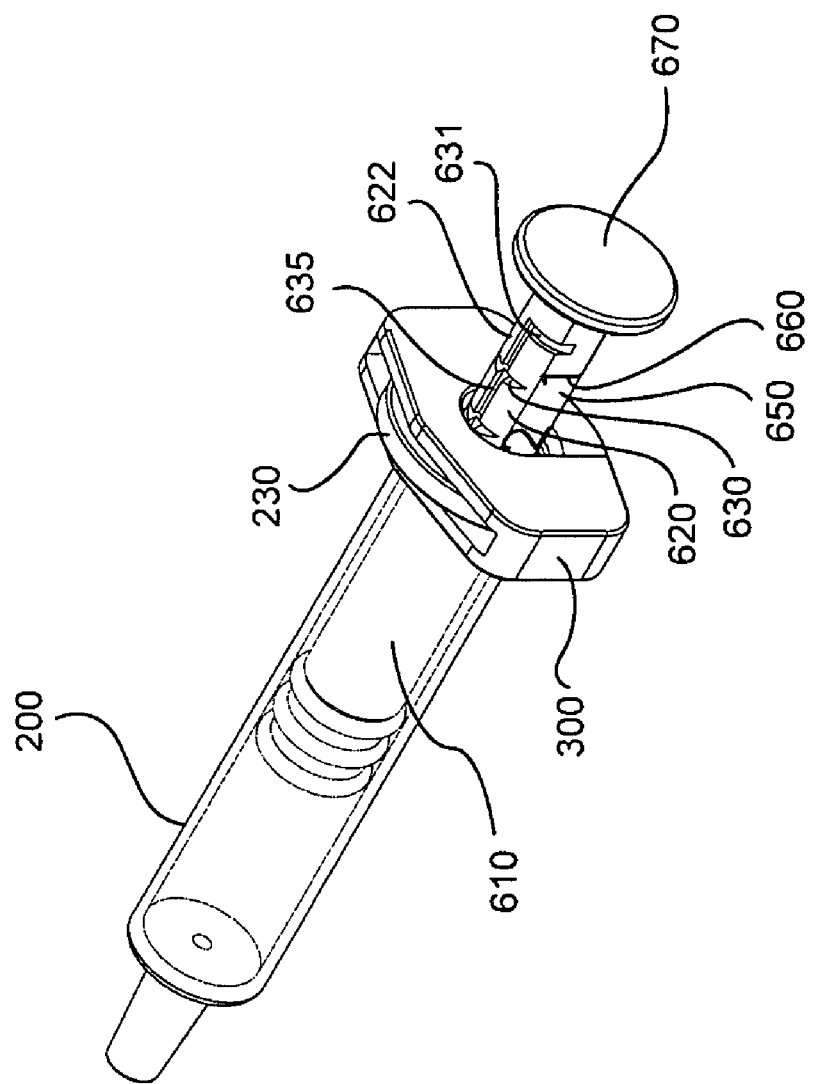
FIG. 12 illustrates a perspective view of a second embodiment of the medical device wherein the plunger rod is positioned to an intermediate length.
Figure 13:
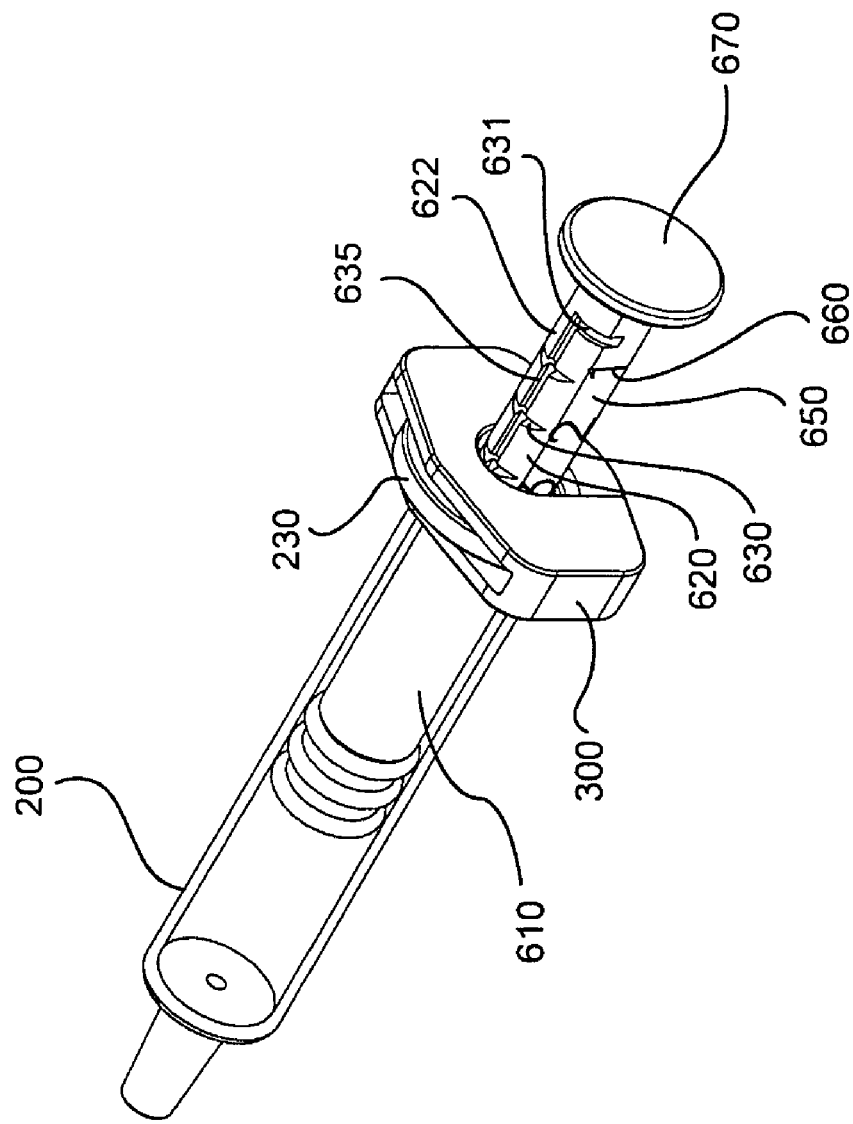
FIG. 13 illustrates a perspective view of a second embodiment of the medical device wherein the plunger rod is positioned to an extended length.

In FIGS. 10-12, the syringe barrel is transparent to show the position of the stopper within the barrel at various locked lengths. It is to be understood that FIGS. 10-12 Figures are for illustration purposes only and the invention should not be limited in any way.

To releasably lock the plunger rod 600 in the compressed position, the proximal portion 620 is advanced distally until it is capable of engaging with the locking depression 631 disposed near the proximal end 622 of the proximal portion.— The proximal portion 620 is then rotated until the protrusions 640, 641 of the distal portion 610 can engage with one or more of the depressions 630 of the proximal portion 620.

To lock the plunger rod 600 into any one of the depressions or stops 630, for example, as indicated by indicia "1", or an intermediate position, as indicated by indicia "2", or an extended position, for example, as indicated at indicia "3", the user applies a proximally directed force to the distal portion 610 of the plunger rod 600 until the detents 643, 644 engage with one of the depressions 630, while the protrusions 640, 641 slide along the narrowed portion 650. To inject the contents of the device, after adjusting the length of the plunger rod 600 to the desired length, the user then applies a force in the distal direction to the plunger rod until the stopper is bottomed out and the entire contents of the device are expelled or the thumbpress 670 and flange (not shown) meet to prevent further movement of the plunger rod 600 in the distal direction. The length of the plunger rod 600 remains at the adjusted position so long as the detents 643, 644 are positioned so that they are not aligned with the track 635.

In an alternative embodiment, the user can apply defined rotational movements to the proximal portion 610 to adjust the length of the plunger rod. For example, in a first rotation position, the complementary protrusions 640, 641 are positioned to fit and slide along narrowed portion 650 within the indentation 635 while the detents 643, 644 are positioned to slide along the narrowed portion 650 of the proximal portion 620 when the length of the plunger rod is being adjusted. This first rotation position, allows the distal and second axial portions 610, 620 to axially slide relative to each other, without locking. Engagement of one of more of the depressions or stops 630 and the protrusions 640, 641 severs the alignment of the protrusions 640, 641 and the indentation 635 and forms the second rotation position.

In embodiments which utilize rotational movements, to deploy the plunger rod into an extended or intermediate locked length, the user would rotate the proximal portion 620 to the first rotation position to disengage the protrusions 640, 641 from the locking depression 631 and align the protrusions 640, 641 with the indentation 635. The first rotation position allows adjustment of the axial position of the distal and proximal portions 610, 620. To adjust or lock the length of the plunger rod 600 to a locked length or extended state, the proximal portion 620 is rotated to the second rotation position so that the protrusions 640, 641 of the distal portion 610 engage one or more of the depressions or stops 630 of the proximal portion 620.

In another embodiment, the distal portion comprises a plurality of grooves or depressions, while the proximal portion comprises a tab which engages one of the grooves. In a further embodiment, the distal portion rotates relative to the proximal portion. In specific embodiments, the distal and proximal portions are capable of being rotated relative to each other to multiple, fixed rotation positions.

A third embodiment is shown in FIGS. 14-18, which utilizes a ratchet-like system to adjust the length of the plunger rod 700 by increments. The length of the plunger rod 710 is adjusted without the use of rotational forces. The plunger rod 700 includes a female portion 710, having a distal end 711 and a proximal end 712, and a male portion 720, having a distal end 721 and a proximal end 722. The female portion 710 and male portion 720 engage to adjust the length of the plunger rod 700. A plurality of teeth 730 are spaced axially along the length of the male portion 720 and a thumbpress (not shown) at the proximal end of the male portion 720. In the embodiment show in FIGS. 14-18, the thumbpress is covered by a thumbpress cap 800. The male portion 720 further includes an flat 750 which also includes indicia or markers 760 disposed thereon for indicating the amount of fluid expelled from the syringe when operated with a plunger rod having a specified length. The markers 760 in the embodiment shown correspond to the teeth 730 disposed on the axial portion of the male portion 720.

The female portion 710 of the alternate embodiment shown in FIGS. 14-18 includes a tab 740 at its distal end 712, which cooperate with a stop 780 on the female portion 720 to prevent accidental separation of the plunger rod portions 710, 720. The female portion 710 also includes complementary catches 743, 744 which engage with the one of the teeth 730 of the male portion 720 to adjust the length of the plunger rod 700.

Figure 14:
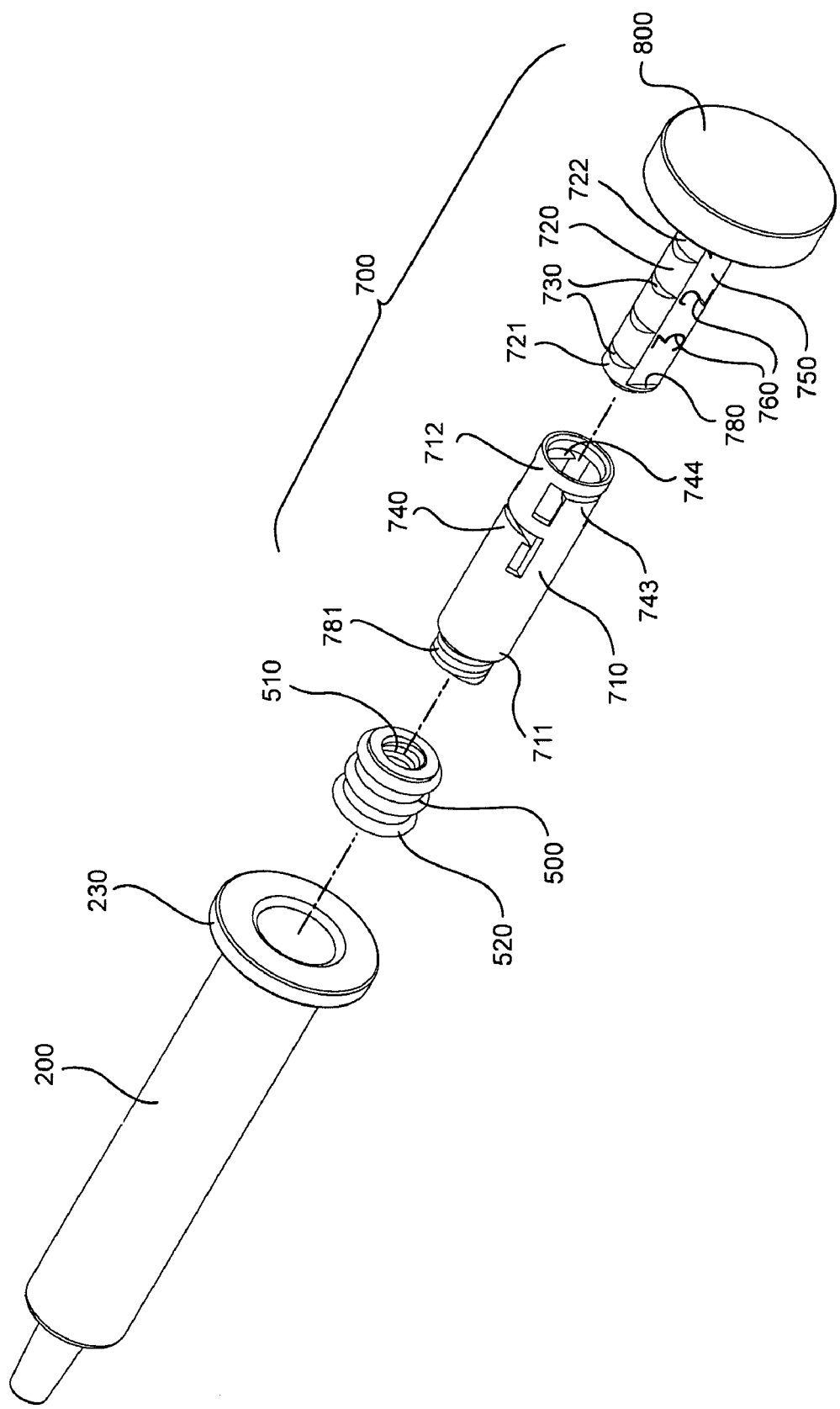
FIG. 14 shows a disassembled perspective view of a medical device according to a third embodiment of the invention.
Figure 15:
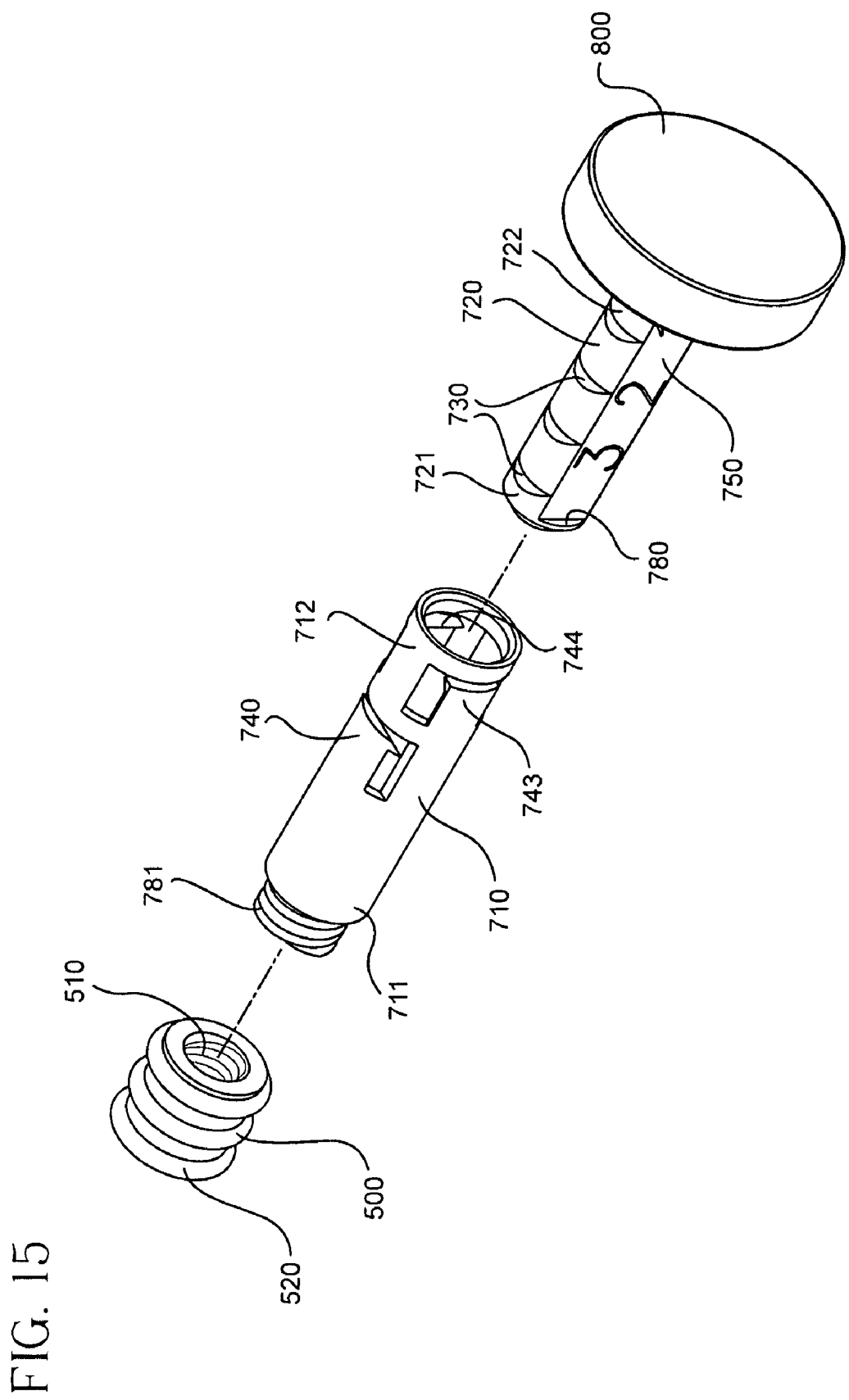
FIG. 15 shows a disassembled perspective view of the plunger rod of FIG. 14, positioned for use.
Figure 16:
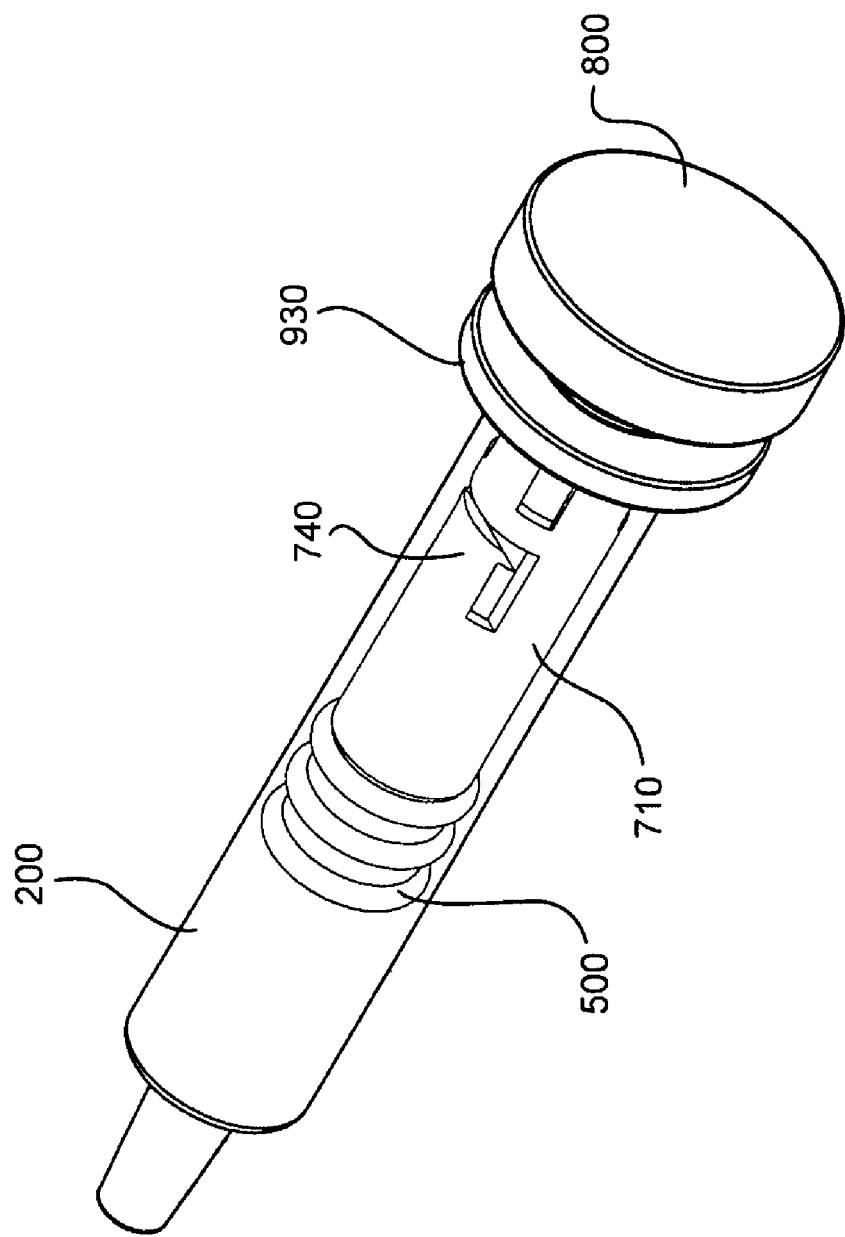
FIG. 16 illustrates a perspective view of a third embodiment of the medical device of FIG. 15, wherein the plunger rod is positioned to compressed length.

To assemble the device prior to packaging, as shown in FIG. 14, the male portion 720 is positioned relative to the female portion 710 to allow the male portion 720 to slide into the female portion 710 by aligning the complementary catches 743,744 with the flat 750 and aligning the tab 740 with the teeth 730. The tab 740 of the female portion 710 is adapted to move past the teeth 730 of the male portion while the catches 743, 744, are adapted to engage with the teeth 730. After fully inserting the male portion 720 into the female portion 710, the plunger rod 700 is locked in the compressed position, as show in more clearly in FIG. 16, by rotating one or both the male portion 710 and female portion 720 to engage the catches 743,744 with one of the teeth 730 disposed closes to the proximal end 722 of the male portion 720.

Figure 17:
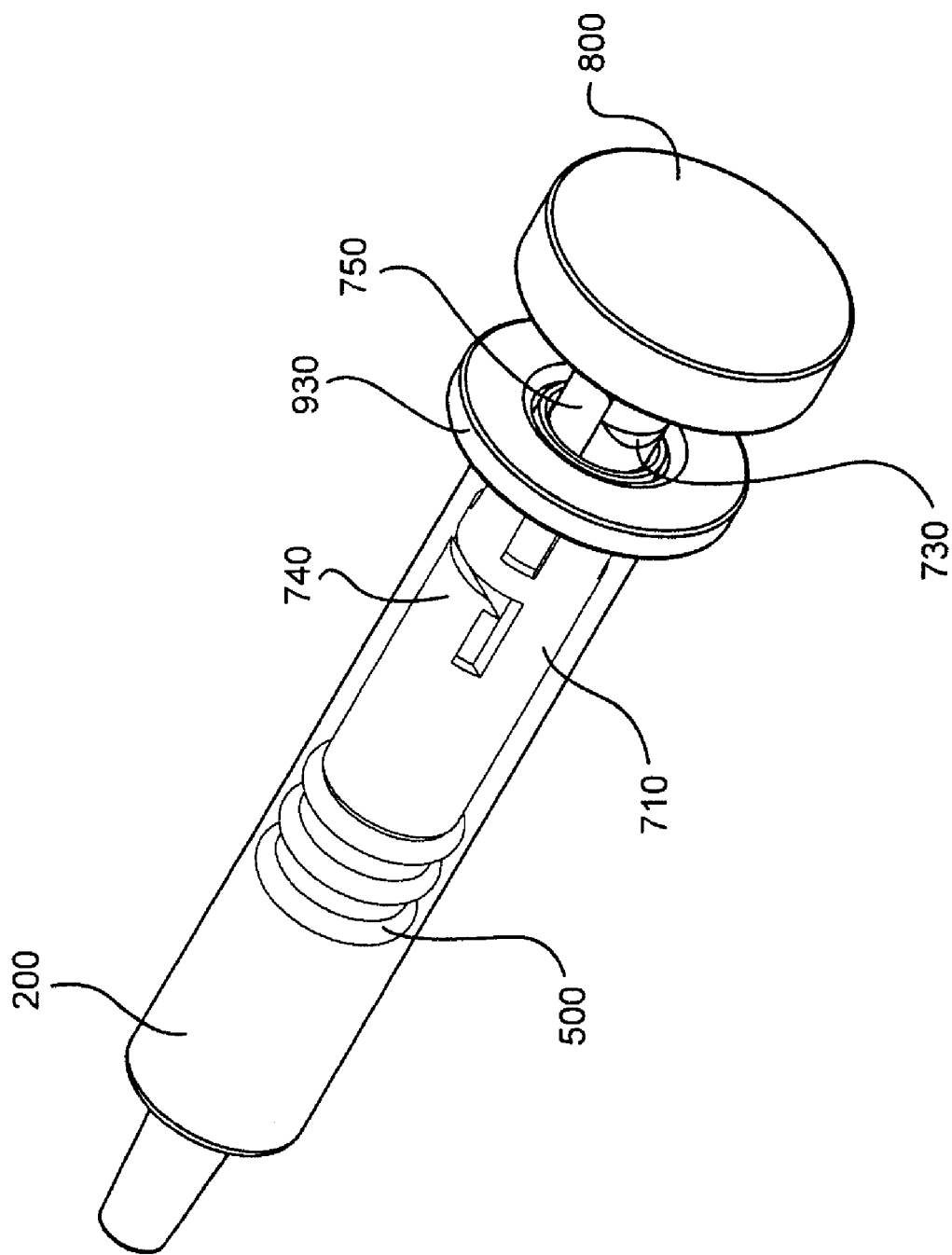
FIG. 17 illustrates a perspective view of a third embodiment of the medical device of FIG. 15, wherein the plunger rod is positioned to an intermediate length.
Figure 18:
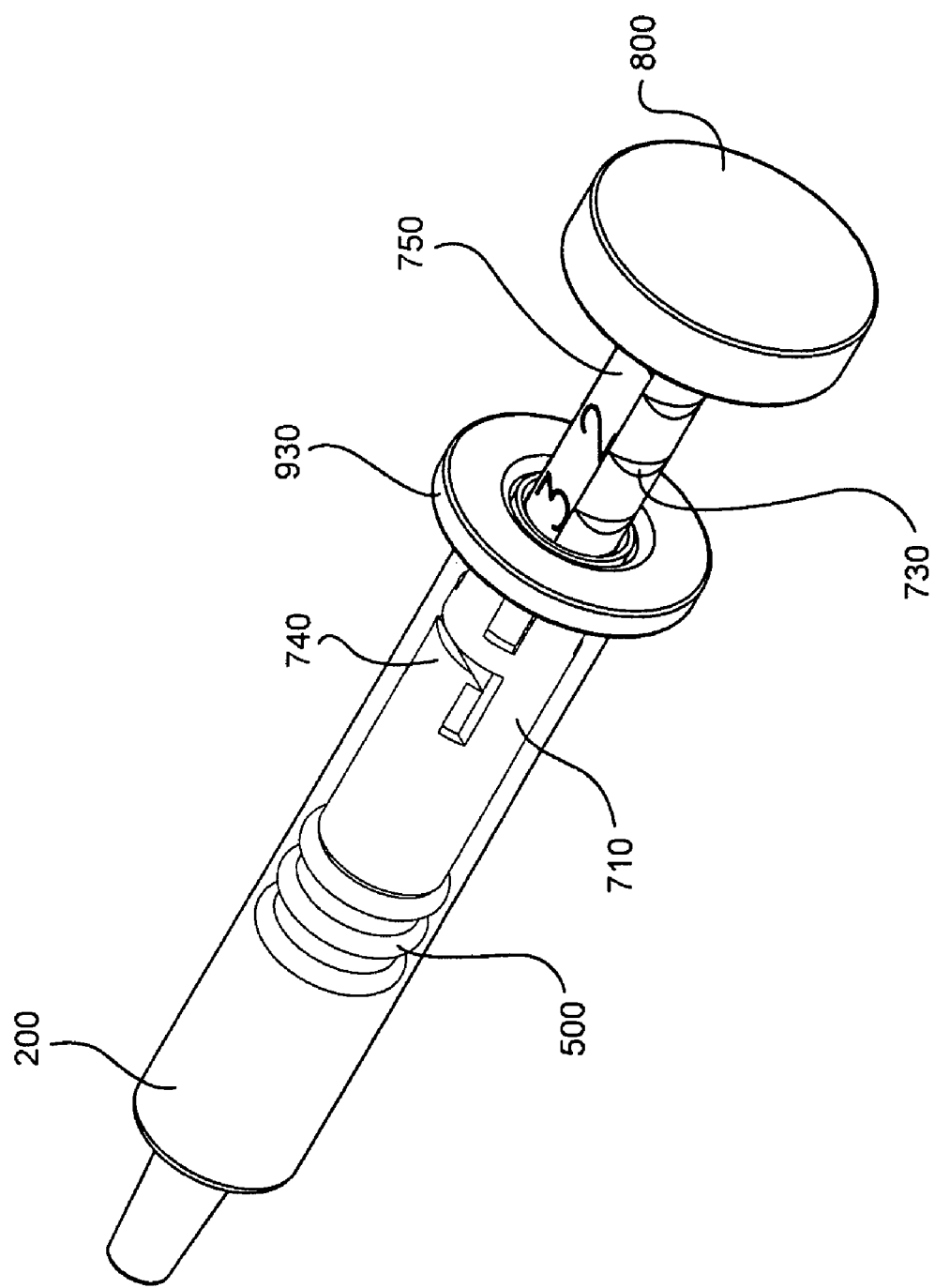
FIG. 18 illustrates a perspective view of a third embodiment of the medical device of FIG. 15, wherein the plunger rod is positioned to an extended length.

To lengthen the plunger rod 700 to an intermediate or extended length, as shown in FIGS. 17 and 18, respectively, a force in the proximal direction is applied to the male portion 720. The teeth 730 move past the catches 743, 744, thereby allowing the catches 743,744 to engage with one of the remaining teeth 730 disposed along the length of the male portion 710. The teeth 730 and catches 743, 744 cooperate to incrementally extend the length of the plunger rod 700. In one or more embodiments, the grooves 730 and catches 743, 744 are adapted to function as a ratchet to prevent shortening of the length of the plunger rod 700.

The thumbpress cap 800 of the embodiments show in FIGS. 14-18 is adapted to provide better tactile grip when adjusting the length of the plunger rod or adjusting the dose to be delivered or setting second or subsequent doses in embodiments which allow multiple doses or partial doses. The thumbpress cap 800 is adapted to cover the opening to the chamber 250 of the barrel 200 located at its proximal end 220 to prevent foreign matter from entering the chamber 250. In a specific embodiment, the thumbpress cap 800 covers the flanges and forms a seal around the plunger rod and barrel. The seal would need to be pierced or broken before the plunger can be used and would, therefore, provide evidence of tampering or contamination. The thumbpress cap 800 can also include a locking mechanism which prevents reuse of the medical device. For example, the thumbpress can be adapted to lock the thumbpress with the flanges and prevent axial movement of the plunger rod. The flanges or thumbpress can further include a frangible point, wherein the force required to break the thumbpress cap or locking mechanism exceeds the force required to break the frangible point.

During an injection, an axial force in the distal direction is applied to the plunger rod at the thumb press until the plunger rod is prevented from further axial motion. The plunger rod is prevented from further axial motion when the restricted from further movement by the opening 220 at the proximal end of the syringe barrel 200, which occurs when the plunger rod is in the compressed or intermediate position. In the extended position, the stopper will bottom out on the distal wall of the barrel to prevent further distal axial motion of the plunger rod. Thus, the practitioner can determine the desired amount of fluid to inject by adjusting the plunger rod to the desired length.

Further, it is desirable to have a plunger rod with an adjustable length to permit injection of measured partial doses of a pre-filled syringe. The practitioner can inject a partial dosage with accuracy without first having to expel the unneeded portion. The adjustable length of the plunger rod according to one or more embodiments described herein allows pre-measured doses to be injected.

Figure 19:
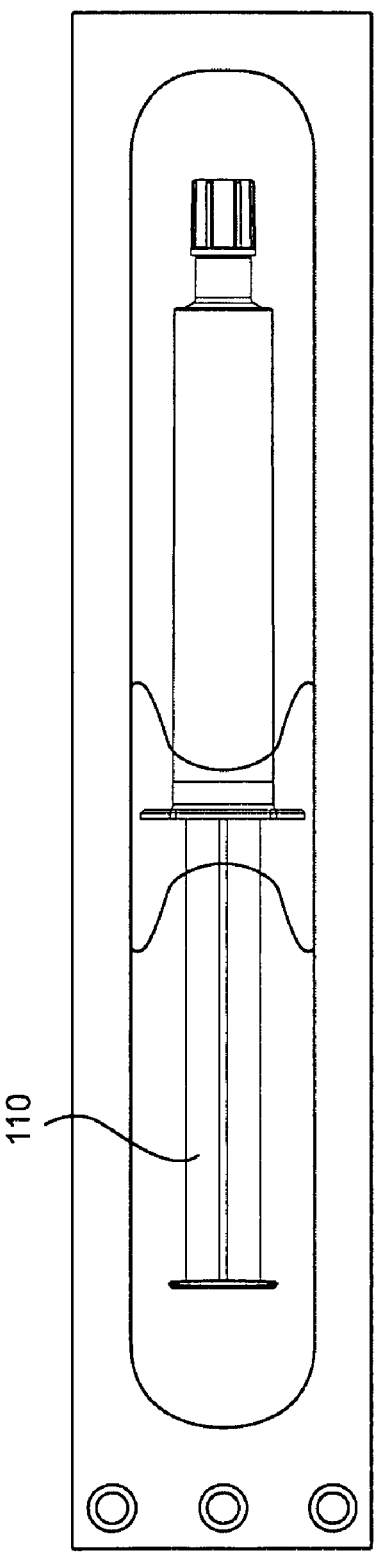
FIG. 19 shows a packaged syringe according to the prior art.

In many instances, syringes are stored in packaging when shipped to users such as hospitals and other medical facilities. Moreover, many syringes can also be pre-filled and therefore, the syringe is not shipped with the plunger rod fully advanced distally with the stopper parked against the distal wall of the syringe problem. To the contrary, many pre-filled syringes that are filled with a fluid such as a flush solution or a medication are shipped with the stopper at the end of the plunger rod located at the proximal end of the syringe barrel with the plunger rod protruding out the distal end of the barrel. Therefore, with a single piece plunger rod assembly of the prior art, as shown in FIG. 19, the packaging must accommodate for these syringes and the elongate plunger rods 110. Such a device requires a relatively long package and large amount of packaging material to accommodate the syringe. Additionally, the overall length of one-piece syringe in FIG. 19 occupies more space, which would occupy additional space in the medical facility. The additional packaging material for the longer syringe results in additional waste to be disposed of after use of the syringe.

Figure 20:
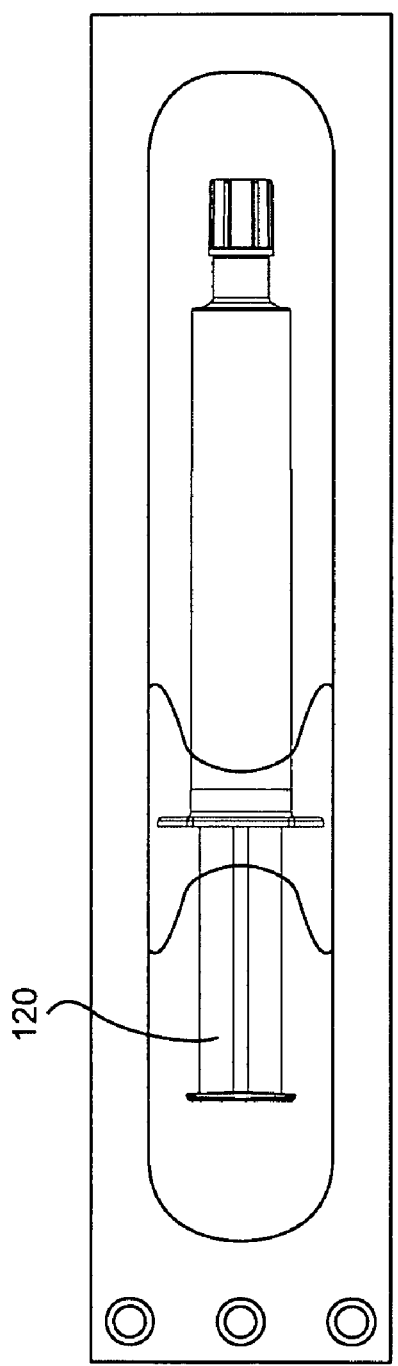
FIG. 20 shows a packaged syringe according to an embodiment of the invention.

According to one or more embodiments of the present invention, the two piece plunger rod can be utilized to conserve packaging or space occupied by the packaged device. This is particularly useful for pre-filled syringes that are pre-filled with fluids such as flush solutions or medications. As shown in FIG. 20, by providing a plunger rod 120 which can be stored or packaged in a compressed position when the stopper at the distal end of the plunger rod is located at the proximal end of the syringe barrel and the plunger rod is extending out the proximal end of the barrel, the overall length of the packaged product and amount of packaging material required to package the product is significantly reduced. In this compressed position, the overall length of the packaged product and amount of packaging material required to package the product is significantly reduced. Thus, according to one or more embodiments, less space is occupied during storage, less packaging material is used for packaged syringes, and less waste is generated after use of a packaged syringe.

One or more aspects of the present invention provide for a method of preparing and a method of using a pre-filled syringe according to one or more of the embodiments disclosed herein. According to one or more embodiments, the method for preparing a pre-filled syringe includes closing the opening in the distal wall of the barrel and filling the barrel with fluid. The method for preparing a pre-filled syringe further includes assembling the plunger rod in a compressed position and attaching the stopper to the distal end of the plunger rod, inserting the plunger rod inside the barrel at its proximal end until the stopper forms a fluid-tight seal with the inside surface of the barrel and the amount of air in the chamber is minimized. According to one or more embodiments, the method of preparing further includes placing the pre-filled syringe in packaging in the compressed position. In a specific embodiment, the fluid is a medical flush solution. In a more specific embodiment, the fluid comprises medication.

In one embodiment, preparing the syringe for use or injection includes removing the prefilled syringe from the packaging; adjusting the length of the plunger rod, injecting or expelling of the contents of the syringe by applying a continuous axial force on the plunger rod in the distal direction until the plunger rod is prevented from moving in the distal direction. In one embodiment, the plunger rod is prevented from moving in the distal direction when the stopper is in contact with the distal wall of the syringe or bottomed. Another embodiment includes injecting or expelling of the contents of the syringe by applying a continuous axial force on the plunger rod in the distal direction until the thumb press is restricted from further movement in the distal direction by the opening at the proximal end of the syringe barrel.

The fluid injected or expelled according to one or more embodiments includes a medical flush solution. Further embodiments provide for method of using a syringe prefilled with fluid comprising medication.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device comprising:
a syringe barrel having a side wall with an inside surface defining a chamber for retaining fluid, an open proximal end and a distal end including a distal wall having a passageway therethrough in fluid communication with the chamber, the open proximal end including a peripheral flange; and
an elongate plunger rod disposed within the barrel, the plunger rod comprising a distal portion, a proximal portion, and a stopper disposed on a distal end of the distal portion, the stopper having a distal face and a proximal end, the proximal portion of the plunger rod slidably mounted to the distal portion so that the overall length of the plunger rod is reversibly adjustable to a plurality of different locked lengths between a compressed locked length and a fully extended length, thereby permitting varying amounts of fluid to be expelled from the barrel corresponding to the plurality of locked lengths,
wherein one of the distal portion or proximal portion slidably receives the other of the distal portion or proximal portion,
wherein the one or the other of the distal portion or proximal portion is hollow and the other of the distal portion or proximal portion is sized to be inserted into the hollow portion, and
wherein the distal portion is hollow and the proximal portion includes a plurality of depressions spaced axially along the proximal portion that cooperate with a tab disposed on the distal portion to provide a plurality of locked positions and to provide a plunger rod that can have a plurality of locked lengths.

2. The medical device of claim 1, wherein each depression comprises a notch having a ramped surface and a stop face which engages the tab when the plunger rod is in a locked position.

3. The medical device of claim 2, further comprising indicia on the plunger rod that indicates the amount of fluid to be dispensed from the syringe when the plunger rod is advanced distally.

4. A medical device comprising:
a syringe barrel having a side wall with an inside surface defining a chamber for retaining fluid, an open proximal end and a distal end including a distal wall having a passageway therethrough in fluid communication with the chamber, the open proximal end including a peripheral flange; and
an elongate plunger rod disposed within the barrel, the plunger rod comprising a distal portion, a proximal portion, and a stopper disposed on a distal end of the distal portion, the stopper having a distal face and a proximal end, the proximal portion of the plunger rod slidably mounted to the distal portion so that the overall length of the plunger rod is reversibly adjustable to a plurality of different locked lengths between a compressed locked length and a fully extended length, thereby permitting varying amounts of fluid to be expelled from the barrel corresponding to the plurality of locked lengths,
wherein the plunger rod further comprises a proximal end including a thumbpress and a thumbpress cap covering the thumbpress.

5. The medical device of claim 4, wherein the thumbpress cap is adapted to lock the thumbpress with the peripheral flange.

6. A medical device comprising:
a syringe barrel having a side wall with an inside surface defining a chamber for retaining fluid, an open proximal end and a distal end including a distal wall having a passageway therethrough in fluid communication with the chamber, the open proximal end including a peripheral flange; and
an elongate plunger rod disposed within the barrel, the plunger rod comprising a distal portion and proximal portion disposed in a slidable, nested arrangement, the proximal portion having a thumb press, one of the distal portion or the proximal portion having a projecting tab and the other of the distal portion or proximal portion having a plurality of grooves that cooperate with the tab so that the overall length of the plunger rod is adjustable between a plurality of different locked lengths ranging from a compressed locked length to a fully-extended length so as to permit varying amounts of fluid to be expelled from the syringe barrel based on the adjustable length of the plunger rod,
wherein the distal portion and proximal portion can be rotated with respect to each other, wherein in a first rotation position, the distal portion and proximal portion can be moved axially with respect to each other, and in a second rotation position, the distal portion and proximal portion can be locked to prevent relative axial movement of the distal portion and proximal portion.

7. The medical device of claim 6, wherein the grooves are spaced axially along the proximal portion and the tab is associated with the distal portion.

8. The medical device of claim 7, further comprising indicia associated with each groove to indicate an amount of fluid that will be expelled from the syringe when the thumb press is advanced toward the barrel and prevented from further distal movement.

9. The device of claim 7, wherein the tab comprises a radially-inward projection which fits into at least one of the grooves to prevent relative axial movement of the distal portion and the proximal portion.

10. The device of claim 9, wherein the proximal portion includes an axially extending narrowed portion which permits the tab to slide along the proximal portion and allow the distal portion and proximal portion to be fully extended and compressed with respect to each other, and upon rotation of the proximal portion with respect to the distal portion, to permit the tab to engage at least one of the grooves.

11. The device of claim 6, wherein the device is enclosed within a package.

12. The device of claim 6, wherein the chamber is pre-filled with a fluid selected from a flush solution and a medication.

13. The device of claim 6, further comprising a thumbpress cap covering the thumbpress.

14. The device of claim 13, wherein the thumbpress cap is adapted to form a seal with the peripheral flange.

15. A medical device comprising:
a syringe barrel having a side wall with an inside surface defining a chamber for retaining fluid, an open proximal end and a distal end including a distal wall having a passageway therethrough in fluid communication with the chamber, the open proximal end including a peripheral flange; and
an elongate plunger rod disposed within the barrel, the plunger rod comprising a distal portion and proximal portion being slidable with respect to each other and including means for regulating the overall length of the plunger rod between a compressed locked length and a fully-extended length to permit variable amounts of fluid to be expelled from the syringe, wherein the distal portion and proximal portion can be rotated with respect to each other, wherein in a first rotation position, the distal portion and proximal portion can be moved axially with respect to each other, and in a second rotation position, the distal portion and proximal portion can be locked to prevent relative axial movement of the distal portion and proximal portion, and wherein the plunger rod further comprises a proximal end including a thumbpress and a thumbpress cap covering the thumbpress.

16. The medical device of claim 15, wherein the thumbpress cap is adapted to lock the thumbpress with the peripheral flange.

17. A medical device comprising:

a syringe barrel having a side wall with an inside surface defining a chamber for retaining fluid, an open proximal end and a distal end including a distal wall having a passageway therethrough in fluid communication with the chamber, the open proximal end including a peripheral flange; and an elongate plunger rod disposed within the barrel, the plunger rod comprising a distal portion, a proximal portion, and a stopper disposed on a distal end of the distal portion, the stopper having a distal face and a proximal end, the proximal portion of the plunger rod slidably mounted to the distal portion so that the overall length of the plunger rod is reversibly adjustable to a plurality of different locked lengths between a compressed locked length and a fully extended length, thereby permitting varying amounts of fluid to be expelled from the barrel corresponding to the plurality of locked lengths, wherein a length of axial motion of the plunger rod through the barrel corresponds to a locked position of the plunger rod between a compressed locked length and a fully extended length, and wherein the amount of fluid to be expelled from the barrel corresponds to the length of axial motion of the plunger rod, wherein the length of axial motion of the plunger rod through the barrel is limited by the proximal portion of the plunger rod interfering with a portion of the barrel adjacent the open proximal end thereof, and wherein the proximal portion of the plunger rod comprises a thumbpress for interference contact with the peripheral flange of the barrel.

18. The medical device of claim 6, wherein a length of axial motion of the plunger rod through the barrel is determined by the position of the projecting tab with respect to one of the plurality of grooves, and wherein the amount of fluid to be expelled from the barrel corresponds to the length of axial motion of the plunger rod.

* * * * *